(12) United States Patent
Conradie et al.

(10) Patent No.: US 10,533,193 B2
(45) Date of Patent: Jan. 14, 2020

(54) METHODS FOR BIOSYNTHESIS OF ISOBUTENE

(71) Applicant: INVISTA NORTH AMERICA S.A.R.L., Wilmington, DE (US)

(72) Inventors: Alex Van Eck Conradie, Cleveland (GB); Adriana Leonora Botes, East Cleveland (GB)

(73) Assignee: INVISTA NORTH AMERICA S.A.R.L., Wilmington, DE (US)

( * ) Notice: Subject to any disclaimer, the term of this patent is extended or adjusted under 35 U.S.C. 154(b) by 0 days.

(21) Appl. No.: 14/914,741

(22) PCT Filed: Aug. 5, 2014

(86) PCT No.: PCT/US2014/049807
§ 371 (c)(1),
(2) Date: Feb. 26, 2016

(87) PCT Pub. No.: WO2015/021059
PCT Pub. Date: Feb. 12, 2015

(65) Prior Publication Data
US 2016/0208289 A1     Jul. 21, 2016

Related U.S. Application Data

(60) Provisional application No. 61/862,422, filed on Aug. 5, 2013.

(51) Int. Cl.
| | | |
|---|---|---|
| *C12P 5/02* | (2006.01) | |
| *C12N 1/21* | (2006.01) | |
| *C12N 9/88* | (2006.01) | |
| *C12N 9/12* | (2006.01) | |
| *C12N 9/16* | (2006.01) | |
| *C12N 9/10* | (2006.01) | |

(52) U.S. Cl.
CPC ............... *C12P 5/026* (2013.01); *C12N 9/13* (2013.01); *C12N 9/16* (2013.01); *C12N 9/88* (2013.01); *C12Y 208/02* (2013.01); *C12Y 301/02* (2013.01); *C12Y 402/01017* (2013.01)

(58) Field of Classification Search
None
See application file for complete search history.

(56) References Cited

U.S. PATENT DOCUMENTS

| 8,703,455 | B2 | 4/2014 | Marliere | |
|---|---|---|---|---|
| 8,741,612 | B2 | 6/2014 | Campbell et al. | |
| 8,765,431 | B2* | 7/2014 | Sherman | C12N 9/16 435/166 |
| 9,422,578 | B2 | 8/2016 | Pearlman et al. | |
| 9,422,580 | B2 | 8/2016 | Pearlman et al. | |
| 2011/0091952 | A1* | 4/2011 | Sherman | C12N 9/16 435/166 |
| 2011/0165644 | A1 | 7/2011 | Marliere | |
| 2011/0300597 | A1 | 12/2011 | Burk et al. | |
| 2012/0021478 | A1 | 1/2012 | Osterhout et al. | |
| 2012/0122563 | A1 | 5/2012 | Walker et al. | |
| 2012/0124839 | A1 | 5/2012 | Kalisz et al. | |
| 2012/0225466 | A1 | 9/2012 | Burk et al. | |
| 2013/0189753 | A1 | 7/2013 | Pearlman et al. | |
| 2013/0210104 | A1 | 8/2013 | Pearlman et al. | |
| 2013/0309742 | A1 | 11/2013 | Campbell et al. | |
| 2014/0065686 | A1 | 3/2014 | Marliere | |
| 2014/0141482 | A1* | 5/2014 | Pearlman | C12P 5/026 435/167 |
| 2014/0325709 | A1 | 10/2014 | Plesch et al. | |
| 2015/0037860 | A1 | 2/2015 | Botes et al. | |
| 2015/0079654 | A1 | 3/2015 | Botes et al. | |
| 2015/0291981 | A1* | 10/2015 | Marliere | C12P 5/026 435/167 |
| 2016/0312257 | A1 | 10/2016 | Noguera et al. | |
| 2017/0283809 | A1 | 10/2017 | Guntner | |

FOREIGN PATENT DOCUMENTS

| CN | 102329182 A | 1/2012 |
|---|---|---|
| EP | 2336340 | 6/2011 |
| EP | 2336341 | 6/2011 |
| WO | WO2009/155382 | 12/2009 |
| WO | WO2010/099201 | 9/2010 |
| WO | WO2010001078 A4 | 9/2010 |
| WO | WO 2011/011689 | 1/2011 |
| WO | WO 2011/076261 | 6/2011 |
| WO | WO 2011/076689 | 6/2011 |
| WO | WO 2011/076691 | 6/2011 |
| WO | WO 2011/079314 | 6/2011 |
| WO | WO2011/140171 | 11/2011 |
| WO | WO2012/018624 | 2/2012 |
| WO | WO 2012/052427 | 4/2012 |

(Continued)

OTHER PUBLICATIONS

European Application 12190029.3 filed on Oct. 25, 2012.*
Gehret et al., Terminal Alkene Formation by the Thioesterase of Curacin A Biosynthesis, J. Biol. Chem., 2011, 286, 14445-54.*
Liu et al., Zirconia microbial hollow fibre bioreactor for *Escherichia coli* culture, Ceramics Int., 2010, 36, 2087-93.*
Studier, Protein production by auto-induction in high-density shaking cultures, Protein Expression Purification, 2005, 41, 207-34.*
Guo et al., Protein tolerance to random amino acid change, Proc. Natl. Acad. Sci. USA, 2004, 101, 9205-10.*
Uniprot, Accession No. G0XS42, 2011, www.uniprot.org.*
Engle et al., The crystal structure of enoyl-CoA hydratase complexed with octanoyl-CoA reveals the structural adaptations required for binding of a long chain fatty acid-CoA molecule, J. Mol. Bio., 1998, 275, 847-59.*

(Continued)

*Primary Examiner* — Robert B Mondesi
*Assistant Examiner* — Todd M Epstein
(74) *Attorney, Agent, or Firm* — Robert B. Furr, Jr.; Licata & Tyrrell P.C.

(57) ABSTRACT

The document provides methods for biosynthesizing isobutene using one or more isolated enzymes such as one or more of a hydratase such as an enzyme classified under EC 4.2.1.- and a decarboxylating thioesterase, or using recombinant host cells expressing one or more such enzymes.

17 Claims, 6 Drawing Sheets
Specification includes a Sequence Listing.

(56) References Cited

FOREIGN PATENT DOCUMENTS

| WO | WO2012/174439 | 12/2012 |
|---|---|---|
| WO | WO 2013/007786 | 1/2013 |
| WO | WO 2013/020118 | 2/2013 |
| WO | WO 2013/028519 | 2/2013 |
| WO | WO 2013/040383 | 3/2013 |
| WO | WO2013036812 A1 | 3/2013 |
| WO | WO 2013/057194 | 4/2013 |
| WO | WO2013/082542 | 6/2013 |
| WO | WO 2013/090915 | 6/2013 |
| WO | WO 2013/092567 | 6/2013 |
| WO | WO 2013/150100 | 10/2013 |
| WO | WO 2013/173437 | 11/2013 |
| WO | WO 2013/181647 | 12/2013 |
| WO | WO 2013/192183 | 12/2013 |
| WO | WO 2014/001517 | 1/2014 |
| WO | WO 2014/033129 | 3/2014 |
| WO | WO2013188546 A3 | 3/2014 |
| WO | WO 2014/064198 | 5/2014 |
| WO | WO 2014/085612 | 6/2014 |
| WO | WO 2014/015210 | 11/2014 |

OTHER PUBLICATIONS

Authorized officer Veronique Cornudel, International Search Report/Written Opinion in PCT/US2013/072275 dated Mar. 6, 2014, 12 pages.
Becker et al., "Metabolicflux engineering of L-lysine production in Corynebacterium glutamicum-over expression and modification of G6P dehydrogenase," J Biotechnol, 2007, 132(2):99-109, 11 pages.
Brigham et al., "Engineering Ralstonia eutropha for Production of Isobutanol from Co2, H2, and 02," Advanced Biofuels and Bioproducts, 2012, Chapter 39, 1065-1090, 36 pages.
Buckel et al., "2-Hydroxyacyl-CoA dehydratases, a novel family of molybdenum enzymes," J Inorganic Biochemistry, 2003, 96(1):53, 1 page.
Bugg et al., "The emerging role for bacteria in lignin degradation and bio-product formation," Current Opinion in Biotechnology, 2011, 22(3):394-400, 7 pages.
Foster-Fromme et al., "Biochemical characterization of isovaleryl-CoA dehydrogenase (LiuA) of Pseudomonas aeruginosa and the importance of liu genes for a functional calabolic pathway of methyl-branched compounds," FEMS Microbial Lett, 2008, 286(1):78-84, 7 pages.
Genbank accession No. AAD44196.1, Oct. 15, 1999, 1 page.
Genbank accession No. AAG05403.1, Jan. 31, 2014, 2 pages.
Genbank accession No. AAV40818.1, Feb. 4, 2005, 1 page.
Genbank accession No. AAV40819.1, Feb. 4, 2005, 1 page.
Genbank accession No. AAV40820.1, Feb. 4, 2005, 1 page.
Genbank accession No. BAA21816.1, Aug. 19, 1997, 2 pages.
Genbank accession No. BAA92740, Aug. 1, 2007, 2 pages.
Genbank accession No. CAA32465.1, Jul. 26, 1995, 1 page.
Genbank accession No. CAA32466.1, Jul. 26, 1995, 1 page.
Genbank accession No. CAA42196.1, Oct. 16, 1995, 1 page.
Genbank accession No. CAA99573.1, Nov. 14, 2006, 2 pages.
Genbank accession No. NP_746661, Jun. 27, 2013, 2 pages.
Hermann et al., "Industrial production of amino acids by coryneform bacteria," J Biotechnol, 2003, 104(1-3):155-172, 18 pages.
Jaremko et al., "The initial metabolic conversion of levulinic acid in Cupriavidus necator," J Biotechnol, 2011, 155 (3):293-298, 6 pages.
Kim et al., "Dehydration of (R)-2-hydroxyacyl-CoA to enoyl-CoA in the fermentation of α-amino acids by anaerobic bacteria," FEMS Microbial Rev, 2004, 28(4):455-468, 14 pages.
Kopke et al., "2,3-Butanediol production by acetogenic bacteria, an alternative route to chemical synthesis, using industrial waste gas," App Enviro Microbial, 2011, 77(15):5467-5475, 9 pages.
Lan et al., "ATP drives direct photosynthetic production of 1-bulanol in cyanobacterial," PNAS, 2012, 109(16):6018-6023, 6 pages.

Lee et al., "Conversion of β-methylbutyric acid to β-hydroxy-β-methylbutyric acid by Galactomyces reessii," Appl Environ Microbial, 1997, 63(11):4191-4195, 5 pages.
Lee et al., "Synthesis of pure meso-2,3-butanediol from crude glycerol using an engineered metabolic pathway in *Escherichia coli*," Appl Biochem Biotechnol, 2012, 166(7):1801-1813, 13 pages.
Li et al., "Cupriavidus necator JMP134 rapidly reduces furfural with a Zn-dependent alcohol dehydrogenase," Biodegradation, 2011, 22 (6):1215-1225, 11 pages.
Lim et al., "Amplification of the NADPH-Relaled Genes zwf and gnd for the Oddball Biosynthesis of PHB in an *E. coli* Transformant Harboring a Cloned phbCAB Operon," J Bioscience and Bioengineering, 2002, 93(6):543-549, 7 pages.
Martin et al., "High-titer production of monomeric hydroxyvalerates from levulinic acid in Pseudomonas putida," J Biotechnol, 2009, 139(1):61-67, 7 pages.
Meijnen et al., "Improved p-hydroxybenzoate productoin by engineered Pseudomonas putida S12 by using a mixed-substrate feeding strategy," Appl Microbial Biotechnol, 2011, 90(3):885-893, 9 pages.
Ohashi et al., "Continuous production of lactic acid from molasses by perfusion culture of Lactococcus lactis using a stirred ceramic membrane reactor," J Bioscience and Bioengineering, 1999, 87(5):647-654, 8 pages.
Papanikolaou et al., "Citric acid production by Yarrowia lipolytica cultivated on olive-mill wastewater-based media," Bioresour. Technol., 2008, 99(7):2419-2428, 10 pages
Perez-Pantoja et al., "Metabolic reconstruction of aromatic compounds degradation from the genome of the amazing pollutant-degrading bacterium Cupriavidus necator JMP134," FEMS Microbial Rev., 2008, 32(5):736-794, 59 pages.
Prybylski et al., "Third-generation feed stocks for the clean and sustainable biotechnological production of bulk chemicals: synthesis of 2-hydroxyisobutyric acid," Energy, Sustainability and Society, 2012, 2:11, 9 pages.
Ramsay et al., "Use of a Nylon Manufacturing Waste as an Industrial Fermentation Substrate," Appl Environ Microbial, 1986, 52(1):152-156, 5 pages.
Seedorf et al., The genome of Clostridium kluyveri, a strict anaerobe with unique metabolic features, Proc Nall Acad Sci USA, 2008, 105(6):2128-2133, 6 pages.
Shen et al., "Driving Forces Enable High-Titer Anaerobic 1-Butanol Synthesis in *Escherichia coli*," Appl Environ Microbial., 2011, 77(9):2905-2915, 11 pages.
Van Leeuwen et al., "Fermentative production of isobutene," Appl Microbial Biotechnol, 2012, 93(4):1377-1387, 11 pages.
Wee et al., "Biotechnological production of lactic acid and its recent applications," Food Technol. Biotechnol., 2006, 44 (2):163-172, 10 pages.
Yang et al., "Value-added uses for crude glycerol-a byproduct of biodiesel production," Biotechnology for Biofuels, 2012, 5:13, 10 pages.
Zhang et al., "Genes encoding acyl-CoA dehydrogenase (AcdH) homologues from Streptomyces coelicolor and Streptomyces avermitilis provide insights into the metabolism of small branched-chain fatty acids and macrolide antibiotic production," Microbiology, 1999, 145(9):2323-2334, 12 pages.
Zhuang et al., "Divergence of function in the hot dog-fold enzyme superfamily: the bacterial Thioesterase YciA," Biochemistry, 2008, 47(9):2789-2796, 8 pages.
Daniel et al., "Biochemistry of coenzyme BI2-dependent glycerol and diol dehydratases and organization of the encoding genes," 1999, FEMS Microbiology Reviews, 22: 553-566.
Fukui et al., "Expression and characterization of (R)-specific enoyl coenzyme A hydratase involved in polyhydroxyalkanoate biosynthesis by Aeromonas caviae," J. Bacteriology, Feb. 1998, 180(3):667-673.
Gehret et al., "Terminal alkene formation by the thioesterase of curacin A biosynthesis: structure of a decarboxylating thioesterase," J. of Biological Chem., 2011, 186(16):14445-54.
Genbank accession No. EIXUJ2.I. Sep. 5, 2012, 2 pages.
Gu et al., "Polyketide Decarboxylative chain Termination Preceded by 0-sulfonation in curacin A Biosynthesis," J. Am. Chemical Soc., Nov. 2009, 131(44):16033-16035.

(56) References Cited

OTHER PUBLICATIONS

International Preliminary Report on Patentability in International Application No. PCT/US2013/045430, dated Dec. 16, 2014, 12 pages.
International Preliminary Report on Patentability and Written Opinion for PCT/US2013/072275, dated Jun. 2, 2015, 8 pages.
International Search Report and Written Opinion in Application No. PCT/US2014/048606, dated Oct. 31, 2014, 19 pages.
International Search Report and Written Opinion in Application No. PCT/US2014/049807, dated Nov. 5, 2014, 56 pages.
Jin et al., "The selective addition of water to C=C bonds; enzymes are the best chemists," Chem Commun., 2011, 47:2502-2510.
Kelada et al., "Delta-aminolevulinic acid dehydratase genotype and lead toxicity: A Huge Review," Am. J. Epidemiology, 2001, 154(1)1-13.
Luddeke et al. "Geraniol and Geranial Dehydrogenases Induced in Anaerobic Monoterpene Degradation by Castellaniella defragrans," Appl. and Environmental Microbiology, 2012, 78(7): 2128-2136.
Luddeke et al.,"Enantiospecific (S)-(+)-linalool formation from beta-myrcene by linalool dehydratase-isomerase," Z Naturforsch C., Jul./Aug. 2011, 66c, 409-12.
Martin et al., "Engineering a mevalonate pathway in *Escherichia coli* for production of terpenoids," Nature Biothechnology, Jul. 2003, 21(7):796-802.
McCarthy et al., "Structural basis of functional group activation by sulfotransferases in complex metabolic pathways," ACS Chem. Biol., 2012, 7:1994-2003.
Rude et al., "Terminal olefin (1-alkene) biosynthesis by a novel p450 fatty acid decarboxylase from J eotgalicoccus speciesm," Appl. Envi ron. Microbiol., 2011, 77 (5):1718-27.
Toraya, "Radical catalysis of B12 enzymes: structure, mechanism, inactivation and reactivation of diol and glycerol dehydratases," Cellular and Molecular Life Sciences, 2000, 105-27.
Uniprot Accession No. 13RA72, Sep. 5, 2012, 2 pages.
U.S. Final Office Action in U.S. Appl. No. 13/691,623, dated Dec. 9, 2014, 15 pages.
U.S. Final Office Action in U.S. Appl. No. 13/524,973, dated Dec. 22, 2014, 24 pages.
U.S. Non-Final Office Action in U.S. Appl. No. 13/691,623, dated Jun. 25, 2014, 13 pages.
U.S. Non-Final Office Action in U.S. Appl. No. 13/524,973, dated Jun. 11, 2014, 17 pages.
Barta et al., "Structural basis for nucleotide binding and reaction catalysis in mevalonate diphosphate decarboxylase," Biochemistry, 51(28):5611-5621, Epub Jul. 6, 2012.
Brodkorb et al., "Linalool dehydratase-isomerase, a bifunctional enzyme in the anaerobic degradation of monoterpenes," J Biol Chem., 285(40):30436-30442, 2010.
Buckel et al., "Glutaconate CoA-transferase from Acidaminococcus fermentans," Eur J Biochem., 118(2):315-321, Aug. 1981.
Chayabutra and Ju, "Degradation of n-hexadecane and its metabolites by Pseudomonas aeruginosa under microaerobic and anaerobic denitrifying conditions," Ar;ml Environ Microbiol., 66(2):493-498, Feb. 2000.
Chung and Rhee, "Overexpression of the (R)-specific enoyl-CoA hydratase gene from Pseudomonas chlororaphis HS2 l in Pseudomonas strains for the biosynthesis of polyhydroxyalkanoates of altered monomer composition," Biosci. Biotechnol. Biochem., 76, 613-16, 2012.
Dhe-Paganon et al., "Mechanism of mevalonate pyrophosphate decarboxylase: evidence for a carbocationic transition state," Biochemist. !}., 33(45):13355-13362, Nov. 15, 1994.
Eikmanns and Buckel, "Crystalline green 5-hydroxyvaleryl-CoA dehydratase from Clostridium aminovalericum," Eur. J. Biochem., 197(3):661-668, May 8, 1991.
Ferrandez et al., "Genetic characterization and expression in heterologous hosts of the 3-(3-hydroxyphenyl)propionate catabolic pathway of *Escherichia coli* K-12," J. Bacteriol., 179(8): 2573-2581, Apr. 1997.

Gogerty and Bobik, "Formation of isobutene from 3-hydroxy-3-methylbutyrate by diphosphomevalonate decarboxylase," Appl Environ Microbiol., 76(24):8004-8010, Epub Oct. 22, 2010.
Guan et al., "Cytochrome P450-dependent desaturation oflauric acid: isoform selectivity and mechanism of formation of 11-dodecenoic acid," Chem Biol Interact., 110(1-2):103-21, 1998.
He and Spain, "A novel 2-aminomuconate deaminase in the nitrobenzene degradation pathway of Pseudomonas pseudoalcaligenes JS45," J Bacteriol., 180(9):2502-2506, 1998.
International Preliminary Report on Patentability and Written Opinion for PCT/US2012/042757, dated Dec. 17, 2013, 7 pages.
International Preliminary Report on Patentability and Written Opinion for PCT/US2012/064407, dated May 13, 2014, 8 pages.
International Preliminary Report on Patentability and Written Opinion for PCT/US2012/067463, dated Jun. 3, 2014, 12 pages.
International Search Report in Application No. PCT/US2012/042757 dated Mar. 6, 2013, 5 pages.
International Search Report in Application No. PCT/US2012/064407, dated Feb. 7, 2013, 13 pages.
International Search Report in Application No. PCT/US2012/067463, dated Jun. 17, 2013, 19 pages.
International Search Report and Written Opinion in Application No. PCT/US2013/045430, dated Feb. 3, 2014, 20 pages.
Invitation to pay additional fees and, where applicable, protest fee for PCT/US2012/067463, dated Mar. 13, 2013, 17 pages.
Jang et al., "Bio-based production of C2—C6 platform chemicals," Biotechnol Bioeng., 109(10):2437-2459, Epub Jul. 13, 2012.
Kasai et al., "Uncovering the protocatechuate 2,3-cleavage pathway genes," J Bacteriol., 191(21):6758-6768, Epub Aug. 28, 2009.
Kim et al., "An allylic ketyl radical intermediate in clostridial amino-acid fermentation," *Nature.*, 452(7184):239-242, Mar. 2008.
Kim, "On the enzymatic mechanism of 2-hydroxyisocaproyl-CoA dehydratase from Clostridium difficile," 2004, Ph.D. dissertation, Philipps-Universitat, Marburg, 2004.
Kizer et al., "Application of Functional Genomics to Pathway Optimization for Increased Isoprenoid Production," Ar;mlied and Environmental Microbiology, 2008, 74(10):3229-3241.
Kuzma et al., "Bacteria produce the volatile hydrocarbon isoprene," Curr Microbiol., 1995 30(2):97-103.
Kuzuyama, "Mevalonate and nonmevalonate pathways for the biosynthesis of isoprene units," Biosci Biotechnol Biochem., 66(8):1619-1627, Aug. 2002.
Liu et al., "Microbial production of R-3-hydroxybutyric acid by recombinant *E. coli* harboring genes of phbA, phbB, and tesB," Ar;ml Microbiol Biotechnol., 76(4):811-818, Epub Jul. 4, 2007.
Luo et al., "Production of 3-hydroxypropionic acid through propionaldehyde dehydrogenase PduP mediated biosynthetic pathway in Klebsiella pneumoniae," Bioresour Technol., 103( 1): 1-6, Epub Oct. 2012.
Mo et al., "Biosynthesis of the allylmalonyl-CoA extender unit for the FK506 polyketide synthase proceeds through a dedicated polyketide synthase and facilitates the mutasynthesis of analogues," J. Am. Chem. Soc., 133, 976-85, 2011.
Morrone et al., "Increasing diterpene yield with a modular metabolic engineering system in *E. coli*: comparison of MEV and MEP isoprenoid precursor pathway engineering," *Applied Microbiology and Biotechnology*, 2010, 85:1893-1906.
Muraki et al., "Prokaryotic homologs of the eukaryotic 3-hydroxyanthranilate 3,4-dioxygenase and 2-amino-3-carboxymuconate-6-semialdehyde decarboxylase in the 2-nitrobenzoate degradation pathway of Pseudomonas fluorescens strain KU-7," *Appl* Environ Microbiol., 69(3): 1564-1572, Mar. 2003.
Prather et al., "De nova biosynthetic pathways: rational design of microbial chemical factories," 2008, 19:468-474.
Rettie et al., "CYP4 Isozyme Specificity and the Relationship between co-Hydroxylation and Terminal Desaturation of Valproic Acid," Biochemistry, 34(24): 7889-7895 (1995).
Schafer et al., "Synthesis of short-chain diols and unsaturated alcohols from secondary alcohol substrates by the Rieske nonheme mononuclear iron oxygenase MdpJ.," Appl Environ Microbiol., 201278(17):6280-6284, Epub Jun. 29, 2012.
Scherf and Buckel, "Purification and properties of an iron-sulfur and FAD-containing 4-hydroxybutyryl-CoA dehydratase/vinylacetyl-

(56) References Cited

OTHER PUBLICATIONS

CoA delta 3-delta 2-isomerase from Clostridium aminobutyricum," Eur J Biochem., 215(2):421-429, Jul. 15, 1993.
Scherf et al., "Succinate-ethanol fermentation in Clostridium kluyveri: purification and characterisation of 4-hydroxybutyryl-CoA dehydratase/vinylacetyl-CoA delta 3-delta 2-isomerase," Arch Microbiol., 161(3):239-245, 1994.
Silver and Fall, "Characterization of aspen isoprene synthase, an enzyme responsible for leaf isoprene emission to the atmosphere," J Biol Chem., 270(22):13010-13016, Jun. 2, 1995.
Sweeney et al., "Physiologically based pharmacokinetic modeling of 1,3-butadiene, 1,2-epoxy-3-butene, and 1,2:3,4-diepoxybutane toxicokinetics in mice and rats," *Carcinogenesis.*, 18(4):611-625, 1997.
Tseng et al., "Biosynthesis of chiral 3-hydroxyvalerate from single propionate-WITelated carbon sources in metabolically engineered *E. coli,*" Microb Cell Fact., 9:96, Nov. 27, 2010.
Tsuge et al., "Molecular characterization and properties of (R)-specific enoyl-CoA hydratases from Pseudomonas aeruginosa: metabolic tools for synthesis of polyhydroxyalkanoates via fatty acid beta-oxidation," Int J Biol Macromol., 31(4-5): 195-205, 2003.
Ulmer et al., "Bacterial production of poly(.beta.-hydroxyalkanoates) containing unsaturated repeating units by Rhodospirillum rubrum," Macromolecules, 27, 1994, 1675-79.
Uniprot Accession No. B8ZLF3, Jun. 15, 2010, 2 pages.
Uniprot Accession No. P32377, Jun. 15, 2010, 4 pages.
Uniprot Accession No. Q7CCL9, Jun. 15, 2010, 2 pages.
Upton and Mckinney, "Role of the methylcitrate cycle in propionate metabolism and detoxification in *Mycobacterium smegmatis,*" Microbiology, 153(Pt 12):3973-3982, Dec. 2007.
Wang and Liao, "Alteration of product specificity of Rhodobacter sphaeroides phytoene desaturase by directed evolution," J Biol Chem., 276(44):41161-41164, Epub Aug. 28, 2001.
Wendt et al., "Crystal structure of the carboxyltransferase subunit of the bacterial sodium ion pump glutaconyl-coenzyme A decarboxylase," EMBO J., 22(14):3493-3502, Jul. 15, 2003.
White, "Butadiene production process overview," Chem Biol Interact., 166(1-3):10-14, Epub Jan. 26, 2007.
Yang et al., "Enhancing production of bio-isoprene using hybrid MVA pathway and isoprene synthase in *E. coli,*" PLoS One, Apr. 2012, 7:1-7.
Zhao et al., "Biosynthesis of isoprene in *Escherichia coli* via methylerythritol phosphate (MEP) pathway," A1mlied Microbilogy and Biotechnology, Apr. 2011, 90: 1915-22.
"Production of butadiene," China Synthetic Rubber Industry, Special issue of 1978, 21 pages (with partial English translation).
U.S. Non-Final Office Action in U.S. Appl. No. 13/916,156, dated Jul. 14, 2015, 35 pages.
U.S. Non-Final Office Action in U.S. Appl. No. 13/524,973, dated Jul. 23, 2015, 24 pages.
Chinese Office Action in Chinese Application No. 201280040122.2, dated Jul. 17, 2015, 7 pages.
International Search Report and Written Opinion in Application No. PCT/US2014/049786, dated Sep. 11, 2015, 17 pages.
International Preliminary Report on Patentability in Application No. PCT/US2014/049786, dated Feb. 9, 2016.
International Preliminary Report on Patentability in Application No. PCT/US2014/048606, dated Feb. 2, 2016.
Office Communication dated Oct. 9, 2014 in U.S. Appl. No. 14/092,115, filed Nov. 27, 2013.
Office Communication dated Apr. 1, 2015 in U.S. Appl. No. 14/092,115, filed Nov. 27, 2013.
Office Communication dated Feb. 2, 2016 in U.S. Appl. No. 14/092,115, filed Nov. 27, 2013.
Office Communication dated Mar. 21, 2016 in U.S. Appl. No. 14/092,115, filed Nov. 27, 2013.
Office Communication dated Jul. 7, 2016 in U.S. Appl. No. 14/092,115, filed Nov. 27, 2013.
Office Communication dated Mar. 16, 2015 in U.S. Appl. No. 13/691,623, filed Nov. 30, 2012.
Office Communication dated Apr. 23, 2015 in U.S. Appl. No. 13/691,623, filed Nov. 30, 2012.
Office Communication dated Jul. 17, 2015 in U.S. Appl. No. 13/691,623, filed Nov. 30, 2012.
Office Communication dated Dec. 7, 2015 in U.S. Appl. No. 13/691,623, filed Nov. 30, 2012.
Office Communication dated May 4, 2016 in U.S. Appl. No. 13/691,623, filed Nov. 30, 2012.
Office Communication dated Dec. 3, 2015 in U.S. Appl. No. 13/916,156, filed Jun. 12, 2013.
Office Communication dated Mar. 15, 2016 in U.S. Appl. No. 13/916,156, filed Jun. 12, 2013.
Office Communication dated Apr. 7, 2016 in U.S. Appl. No. 13/916,156, filed Jun. 12, 2013.
Office Communication dated Apr. 20, 2016 in U.S. Appl. No. 13/916,156, filed Jun. 12, 2013.
Office Communication dated May 17, 2016 in U.S. Appl. No. 13/916,156, filed Jun. 12, 2013.
Office Communication dated Nov. 17, 2015 in EP 12 731 825.1.
Office Communication dated Jun. 6, 2016 in EP 12 799 032.3.
Office Communication dated Aug. 12, 2016 in EP 13 739 305.4.
Office Communication dated Jun. 8, 2016 in CN 201280040122.2.
"Microbiology", Retrieved from the Internet URL: www.britannica.com/science/microbiology, 2017, 8 pages.
Demain et al., "Manual of Industrial Microbiology and Biotechnology", Second Edition, Scale-Up of Microbial Processes, ASM Press, 1999, 5 pages.
Stanbury et al., "Principles of Fermentation Technology", Second Edition, Aeration and Agitation, 1995, 14 pages.

\* cited by examiner

Figure 3

(R)-specific enoyl-CoA hydratase from *Pseudomonas aeruginosa* (encoded by PhaJ1 gene) (GenBank: BAA92740)

```
  1 msqvqnipya elevgqkaey tssiaerdlq lfaavsgdrn pvhldaayaa ttqfkeriah
 61 gmlsgalisa aiatvlpgpg tiylgqtlrf trpvklgddl kvelevlekl pknrvrmatr
121 vfnqagkqvv dgeaeimape eklsvelael ppisig
```

(R)-specific enoyl-CoA hydratase from *Aeromonas punctata* (GenBank: BAA21816.1)

```
  1 msaqslevgq karlskrfga aevaafaals edfnplhldp afaattafer pivhgmllas
 61 lfsgllgqql pgkgsiylgq slsfklpvfv gdevtaevev talredkpia tlttriftqg
121 galavtgeav vklp
```

Acyl dehydratase from *Pseudomonas putida* (GenBank: NP_746661)

```
  1 msqvtntpye alevgqkaey kksveerdiq lfaamsgdhn pvhldaefaa ksmfreriah
 61 gmfsgalisa avactlpgpg tiylgqqmsf qkpvkigdtl tvrleilekl pkfkvriatn
121 vynqndelvv ageaeilapr kqqtvelvsp pnfvas
```

Figure 4

*Lyngbya majuscula* chain A, thioesterase domain from the Curacin biosynthetic pathway (GenBank: 3QIT_A);

```
  1 snameekfle fggnqiclcs wgspehpvvl cihgileqgl awqevalpla aqgyrvvapd
 61 lfghgrsshl emvtsysslt flaqidrviq elpdqplllv ghsmgamlat aiasvrpkki
121 kelilvelpl paeeskkesa vnqlttcldy lsstpqhpif pdvataasrl rqaipslsee
181 fsyilaqrit qpnqggvrws wdaiirtrsi lglnnlpggr sqylemlksi qvpttlvygd
241 ssklnrpedl qqqkmtmtqa krvflsgghn lhidaaaala slilts
```

FIGURE 6

| Sample ID | Analyte | Mwt [g/mol] | Peak Retention Time (mins) [min] | Peak Area @ 260nm (mAu) [mAu] | Observed Mass (m/z) Negative mode [M-H] | Observed Mass (m/z) positive mode [M+H] | Comments |
|---|---|---|---|---|---|---|---|
| 0.1 [mg/mL] crotonyl CoA as standard | Crotonyl-CoA | 835.6 | 5.374 | 1839.89 | 833.7 | 835.9 | |
| Biotransformation at 1 [h] time point | 3-hydroxybutanoyl-CoA | 853.6 | 4.531 | 10197.8 | 851.9 | 854 | Biotransformation undertaken at 1 [mM] substrate concentration. (m/z) corresponds to desired product. |
| | Crotonyl-CoA | 835.6 | 5.37 | 907.59 | 833.9 | 836 | |
| Standard only control 1 [h] time point | 3-hydroxybutanoyl-CoA | 853.6 | 4.529 | 10571.9 | 865.9 | 868.1 | Weak signal in baseline noise of MS. |
| | Crotonyl-CoA | 835.6 | 5.37 | 9.207 | 833.9 | 836 | |

FIGURE 7

| Sample ID | Analyte | Mwt [g/mol] | Peak Retention Time (mins) [min] | Peak Area @ 260nm (mAu) [mAu] | Observed Mass (m/z) Negative mode [M-H] | Observed Mass (m/z) Positive mode [M+H] | Comments |
|---|---|---|---|---|---|---|---|
| 2 [mM] reference standard | 3-methyl-3-hydroxy-butanoyl-CoA | 867.2 | 4.759 | 8596.83 | 865.9 | 868.1 | Acetyl-CoA impurity was formed during substrate preparation. |
| | acetyl-CoA | 809.6 | 4.502 | 5150.72 | 807.9 | 810 | |
| Biotransformation at 1 [h] time point | 3-methyl-3-hydroxy-butanoyl-CoA | 867.2 | 4.783 | 3697.66 | 865.9 | 868.1 | Biotransformation undertaken at 1 [mM] substrate concentration. (m/z) corresponds to desired product. |
| | acetyl-CoA | 809.6 | 4.519 | 2372.45 | 807.9 | 810 | |
| | 3-methyl-but-2-enoyl-CoA | 849.2 | 5.127 | 84.89 | 848 | 850 | |
| Substrate only control at 1 [h] time point | 3-methyl-3-hydroxy-butanoyl-CoA | 867.2 | 4.776 | 3623.56 | 865.9 | 868.1 | no peak/mass corresponding to product |
| | acetyl-CoA | 809.6 | 4.511 | 2275.27 | 807.9 | 810 | |

SEQUENCE LISTING

```
<160> NUMBER OF SEQ ID NOS: 4

<210> SEQ ID NO 1
<211> LENGTH: 156
<212> TYPE: PRT
<213> ORGANISM: Pseudomonas aeruginosa

<400> SEQUENCE: 1

Met Ser Gln Val Gln Asn Ile Pro Tyr Ala Glu Leu Glu Val Gly Gln
1               5                   10                  15

Lys Ala Glu Tyr Thr Ser Ser Ile Ala Glu Arg Asp Leu Gln Leu Phe
                20                  25                  30

Ala Ala Val Ser Gly Asp Arg Asn Pro Val His Leu Asp Ala Ala Tyr
            35                  40                  45

Ala Ala Thr Thr Gln Phe Lys Glu Arg Ile Ala His Gly Met Leu Ser
        50                  55                  60

Gly Ala Leu Ile Ser Ala Ala Ile Ala Thr Val Leu Pro Gly Pro Gly
65                  70                  75                  80

Thr Ile Tyr Leu Gly Gln Thr Leu Arg Phe Thr Arg Pro Val Lys Leu
                85                  90                  95

Gly Asp Asp Leu Lys Val Glu Leu Glu Val Leu Glu Lys Leu Pro Lys
                100                 105                 110

Asn Arg Val Arg Met Ala Thr Arg Val Phe Asn Gln Ala Gly Lys Gln
            115                 120                 125

Val Val Asp Gly Glu Ala Glu Ile Met Ala Pro Glu Glu Lys Leu Ser
        130                 135                 140
```

```
Val Glu Leu Ala Glu Leu Pro Pro Ile Ser Ile Gly
145                 150                 155

<210> SEQ ID NO 2
<211> LENGTH: 134
<212> TYPE: PRT
<213> ORGANISM: Aeromonas punctata

<400> SEQUENCE: 2

Met Ser Ala Gln Ser Leu Glu Val Gly Gln Lys Ala Arg Leu Ser Lys
1               5                   10                  15

Arg Phe Gly Ala Ala Glu Val Ala Ala Phe Ala Ala Leu Ser Glu Asp
                20                  25                  30

Phe Asn Pro Leu His Leu Asp Pro Ala Phe Ala Ala Thr Thr Ala Phe
            35                  40                  45

Glu Arg Pro Ile Val His Gly Met Leu Leu Ala Ser Leu Phe Ser Gly
        50                  55                  60

Leu Leu Gly Gln Gln Leu Pro Gly Lys Gly Ser Ile Tyr Leu Gly Gln
65                  70                  75                  80

Ser Leu Ser Phe Lys Leu Pro Val Phe Val Gly Asp Glu Val Thr Ala
                85                  90                  95

Glu Val Glu Val Thr Ala Leu Arg Glu Asp Lys Pro Ile Ala Thr Leu
            100                 105                 110

Thr Thr Arg Ile Phe Thr Gln Gly Gly Ala Leu Ala Val Thr Gly Glu
        115                 120                 125

Ala Val Val Lys Leu Pro
    130

<210> SEQ ID NO 3
<211> LENGTH: 156
<212> TYPE: PRT
<213> ORGANISM: Pseudomonas putida

<400> SEQUENCE: 3

Met Ser Gln Val Thr Asn Thr Pro Tyr Glu Ala Leu Glu Val Gly Gln
1               5                   10                  15

Lys Ala Glu Tyr Lys Lys Ser Val Glu Glu Arg Asp Ile Gln Leu Phe
                20                  25                  30

Ala Ala Met Ser Gly Asp His Asn Pro Val His Leu Asp Ala Glu Phe
            35                  40                  45

Ala Ala Lys Ser Met Phe Arg Glu Arg Ile Ala His Gly Met Phe Ser
        50                  55                  60

Gly Ala Leu Ile Ser Ala Ala Val Ala Cys Thr Leu Pro Gly Pro Gly
65                  70                  75                  80

Thr Ile Tyr Leu Gly Gln Gln Met Ser Phe Gln Lys Pro Val Lys Ile
                85                  90                  95

Gly Asp Thr Leu Thr Val Arg Leu Glu Ile Leu Glu Lys Leu Pro Lys
            100                 105                 110

Phe Lys Val Arg Ile Ala Thr Asn Val Tyr Asn Gln Asn Asp Glu Leu
        115                 120                 125

Val Val Ala Gly Glu Ala Glu Ile Leu Ala Pro Arg Lys Gln Gln Thr
130                 135                 140

Val Glu Leu Val Ser Pro Pro Asn Phe Val Ala Ser
145                 150                 155

<210> SEQ ID NO 4
<211> LENGTH: 286
```

```
<212> TYPE: PRT
<213> ORGANISM: Lyngbya majuscula

<400> SEQUENCE: 4

Ser Asn Ala Met Glu Glu Lys Phe Leu Glu Phe Gly Gly Asn Gln Ile
1               5                   10                  15

Cys Leu Cys Ser Trp Gly Ser Pro Glu His Pro Val Val Leu Cys Ile
            20                  25                  30

His Gly Ile Leu Glu Gln Gly Leu Ala Trp Gln Glu Val Ala Leu Pro
            35                  40                  45

Leu Ala Ala Gln Gly Tyr Arg Val Val Ala Pro Asp Leu Phe Gly His
        50                  55                  60

Gly Arg Ser Ser His Leu Glu Met Val Thr Ser Tyr Ser Ser Leu Thr
65                  70                  75                  80

Phe Leu Ala Gln Ile Asp Arg Val Ile Gln Glu Leu Pro Asp Gln Pro
                85                  90                  95

Leu Leu Leu Val Gly His Ser Met Gly Ala Met Leu Ala Thr Ala Ile
                100                 105                 110

Ala Ser Val Arg Pro Lys Lys Ile Lys Glu Leu Ile Leu Val Glu Leu
            115                 120                 125

Pro Leu Pro Ala Glu Glu Ser Lys Lys Glu Ser Ala Val Asn Gln Leu
        130                 135                 140

Thr Thr Cys Leu Asp Tyr Leu Ser Ser Thr Pro Gln His Pro Ile Phe
145                 150                 155                 160

Pro Asp Val Ala Thr Ala Ala Ser Arg Leu Arg Gln Ala Ile Pro Ser
                165                 170                 175

Leu Ser Glu Glu Phe Ser Tyr Ile Leu Ala Gln Arg Ile Thr Gln Pro
            180                 185                 190

Asn Gln Gly Gly Val Arg Trp Ser Trp Asp Ala Ile Ile Arg Thr Arg
        195                 200                 205

Ser Ile Leu Gly Leu Asn Asn Leu Pro Gly Gly Arg Ser Gln Tyr Leu
    210                 215                 220

Glu Met Leu Lys Ser Ile Gln Val Pro Thr Thr Leu Val Tyr Gly Asp
225                 230                 235                 240

Ser Ser Lys Leu Asn Arg Pro Glu Asp Leu Gln Gln Gln Lys Met Thr
                245                 250                 255

Met Thr Gln Ala Lys Arg Val Phe Leu Ser Gly Gly His Asn Leu His
                260                 265                 270

Ile Asp Ala Ala Ala Ala Leu Ala Ser Leu Ile Leu Thr Ser
            275                 280                 285
```

METHODS FOR BIOSYNTHESIS OF ISOBUTENE

This application is the National Stage of International Application No. PCT/US2014/049807 filed Aug. 5, 2014, and claims priority to U.S. Provisional Application Ser. No. 61/862,422, filed Aug. 5, 2013, the contents of each of which are incorporated herein by reference in their entirety.

TECHNICAL FIELD

This document relates to methods for biosynthesizing isobutene using one or more isolated enzymes such as one or more of an enoyl-CoA dehydratase, a mevalonate diphosphate decarboxylase, or a decarboxylating thioesterase (TE) such as CurM TE, or using recombinant host cells expressing one or more such enzymes.

BACKGROUND

Isobutene is an important monomer in the manufacture of fuel additives, butyl rubber polymer, and antioxidants (Bianca et al., *Appl. Microbiol Biotechnol.*, 2012, 93, 1377-1387).

Manufacturers of goods using isobutene as feedstock depend on a number of petroleum-based sources, including (i) a C4 stream from a steam cracker separated from the butadiene, (ii) butene-butane fractions from a catalytic cracker and (iii) n-butane (from LPG) that is isomerized to isobutane and dehydrogenated to isobutene.

Given a reliance on petrochemical feedstocks and energy intensive processes, biotechnology offers an alternative approach via biocatalysis. Biocatalysis is the use of biological catalysts, such as enzymes or whole cells, to perform biochemical transformations of organic compounds.

Accordingly, against this background, it is clear that there is a need for sustainable methods for producing intermediates, in particular isobutene, wherein the methods are biocatalysis based. Both bioderived feedstocks and petrochemical feedstocks are viable starting materials for the biocatalysis processes.

SUMMARY

This document is based, at least in part, on constructing efficient biochemical pathways for producing 3-methyl-3-hydroxy-butyrate, which can be converted to isobutene by a mevalonate diphosphate decarboxylase or a decarboxylating thioesterase such as CurM TE. Such pathways rely on a R-specific enoyl-CoA hydratase to introduce the (R)-3-hydroxy functional group into 3-methyl-but-2-enoyl-CoA. Prior to the present invention, it was not known that an enzyme capable of introducing a (R)-3-hydroxy group into 3-methyl-but-2-enoyl-CoA could be utilized for the biological synthesis of 3-hydroxy-3-methylbutyrate. Also, as described herein, activation of 3-methyl-3-hydroxybutyrate substrate with acyl carrier protein and sulphonation of the 3-hydroxyl group allows conversion to isobutene by a decarboxylating thioesterase such as CurM TE.

Thus this document provides pathways and enzymes which can convert either of the central precursors 3-methyl-2-oxobutanoate or 4-methyl-2-oxopentanoate into isobutene via a common intermediate, 3-methyl-3-hydroxy-but-2-enoyl-CoA. As used herein, the term "central precursor" is used to denote any metabolite in any metabolic pathway shown herein leading to the synthesis of isobutene. The term "central metabolite" is used herein to denote a metabolite that is produced in all microorganisms to support growth.

In one aspect, this document features a method for synthesizing isobutene. The method includes forming a vinyl group in 3-methyl-3-hydroxybutanoate using a decarboxylating thioesterase. The decarboxylating thioesterase can be the gene product of CurM TE. The decarboxylating thioesterase can have at least 70% homology to the amino acid sequence set forth in SEQ ID NO:4. The method can be performed using isolated enzymes, using cell lysates comprising the enzymes, or can be performed in a recombinant host. The host can be a prokaryotic host selected from the group consisting of the genus *Escherichia* such as *Escherichia coli*; from the genus Clostridia such as *Clostridium ljungdahlii*, *Clostridium autoethanogenum* or *Clostridium kluyveri*; from the genus Corynebacteria such as *Corynebacterium glutamicum*; from the genus *Cupriavidus* such as *Cupriavidus necator* or *Cupriavidus metallidurans*; from the genus *Pseudomonas* such as *Pseudomonas fluorescens* or *Pseudomonas putida*; from the genus *Bacillus* such as *Bacillus subtillis*; or from the genus *Rhodococcus* such as *Rhodococcus equi*. The host can be a eukaryotic host selected from the group consisting of the genus *Aspergillus* such as *Aspergillus niger*; from the genus *Saccharomyces* such as *Saccharomyces cerevisiae*; from the genus *Pichia* such as *Pichia pastoris*; from the genus *Yarrowia* such as *Yarrowia lipolytica* or from the genus *Issatchenkia* such as *Issathenkia orientalis* or from the genus *Debaryomyces* such as *Debaryomyces hansenii* or from the genus *Arxula* such as *Arxula adenoinivorans* or from the genus *Kluyveromyces* such as *Kluyveromyces lactis*.

The recombinant host can be subjected to a fermentation strategy entailing anaerobic, micro-aerobic or aerobic cultivation. A cell retention strategy using, for example, a ceramic hollow fiber membrane can be used to achieve and maintain a high cell density during fermentation.

The principal carbon source fed to the fermentation derives from biological or non-biological feedstocks. The biological feedstock can be, or can derive from, glycerol, levulinic acid, hemicellulose, cellulose, lignocellulose, lignin, monosaccharides, disaccharides, triglycerides or municipal waste. The non-biological feedstock can be, or can derive from, natural gas, syngas, non-volatile residue (NVR) or other waste stream for either the chemical or petrochemical industries.

This document also features a recombinant host that includes an exogenous nucleic acid encoding a R-specific enoyl-CoA hydratase, a sulfotransferase, and a decarboxylating thioesterase.

The reactions of the pathways described herein can be performed in one or more cell (e.g., host cell) strains (a) naturally expressing one or more relevant enzymes, (b) genetically engineered to express one or more relevant enzymes, or (c) naturally expressing one or more relevant enzymes and genetically engineered to express one or more relevant enzymes. Alternatively, relevant enzymes can be extracted from any of the above types of host cells and used in a purified or semi-purified form. Extracted enzymes can optionally be immobilized to a solid substrate such as the floors and/or walls of appropriate reaction vessels. Moreover, such extracts include lysates (e.g., cell lysates) that can be used as sources of relevant enzymes. In the methods provided by the document, all the steps can be performed in cells (e.g., host cells), all the steps can be performed using extracted enzymes, or some of the steps can be performed in cells and others can be performed using extracted enzymes.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and the drawings, and from the claims. The word "comprising" in the claims may be replaced by "consisting essentially of" or with "consisting of," according to standard practice in patent law.

DESCRIPTION OF DRAWINGS

FIG. 3 is the amino acid sequence of the (R)-specific enoyl-CoA hydratase from *Pseudomonas aeruginosa* (encoded by PhaJ1 gene) (GenBank: BAA92740) (SEQ ID NO: 1); *Aeromonas punctata* (GenBank: BAA21816.1) (SEQ ID NO: 2); and *Pseudomonas putida* (GenBank: NP_746661) (SEQ ID NO: 3).

FIG. 4 is the amino acid sequence of the *Lyngbya majuscula* chain A, thioesterase from the Curacin biosynthetic pathway (GenBank: 3QIT_A) (SEQ ID NO: 4).

FIG. 6 is a table of results for the LC-MS analysis of an enzyme assay in the reverse (dehydrating) direction for an enoyl-CoA hydratase activity encoded by phaJ. The results indicate that the enoyl-CoA hydratase is reversible, favoring the forward hydration reaction.

FIG. 7 is a table of results for the LC-MS analysis of an enzyme assay in the reverse (dehydrating) direction for an enoyl-CoA hydratase encoded by phaJ. The results indicate that the enoyl-CoA hydratase accepted 3-methyl-3-hydroxybutanoyl-CoA as substrate. Given the reversibility of the enzyme reaction, the enoyl-CoA hydratase accepts 3-methyl-3-hydroxybut-2-enoyl-CoA as a substrate.

DETAILED DESCRIPTION

Figure 1:
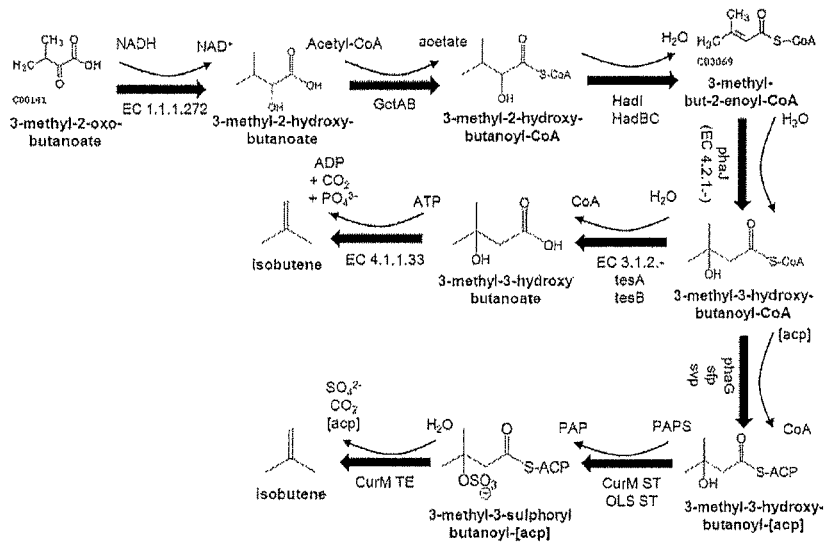
FIG. 1 is a schematic of exemplary biochemical pathways leading to isobutene using 3-methyl-2-oxobutanoate as a central precursor.

In particular, this document provides enzymes and recombinant host microorganisms for isobutene synthesis that can introduce a (R)-3-hydroxy functional group into 3-methyl-but-2-enoyl-CoA, which can in turn be converted after one or more enzymatic steps to isobutene by a MDD or a decarboxylating thioesterase such as CurM TE. As such, host microorganisms described herein can include pathways that can be manipulated such that isobutene can be produced. In an endogenous pathway, the host microorganism naturally expresses all of the enzymes catalyzing the reactions within the pathway. A host microorganism containing an engineered pathway does not naturally express all of the enzymes catalyzing the reactions within the pathway but has been engineered such that all of the enzymes within the pathway are expressed in the host. Within an engineered pathway, the enzymes can be from a single source, i.e., from one species, or can be from multiple sources, i.e., different species.

Nucleic acids encoding the enzymes described herein have been identified from various organisms and are readily available in publicly available databases such as GenBank or EMBL. Any of the enzymes described herein that can be used for isobutene production can have at least 70% sequence identity (homology) (e.g., at least 75%, 80%, 85%, 90%, 95%, 97%, 98%, 99%, or 100%) to the amino acid sequence of the corresponding wild-type enzyme. For example, a (R)-specific enoyl-CoA hydratase described herein can have at least 70% sequence identity (homology) (e.g., at least 75%, 80%, 85%, 90%, 95%, 97%, 98%, 99%, or 100%) to the amino acid sequence of the *Pseudomonas aeruginosa* (R)-specific enoyl-CoA hydratase encoded by PhaJ1 gene (GenBank: BAA92740, SEQ ID NO:1), *Aeromonas punctata* (R)-specific enoyl-CoA hydratase (GenBank: BAA21816.1, SEQ ID NO:2), and *Pseudomonas putida* acyl dehydratase (GenBank: NP_746661, SEQ ID NO:3). For example, a decarboxylating thioesterase described herein can have at least 70% sequence identity (homology) (e.g., at least 75%, 80%, 85%, 90%, 95%, 97%, 98%, 99%, or 100%) to the amino acid sequence of the *Lyngbya majuscula* chain A, thioesterase from the Curacin biosynthetic pathway (GenBank: 3QIT_A, SEQ ID NO:4), *Pseudomonas entomophila* thioesterase (GenBank: YP_610919), *Haliangium ochraceum* thioesterase (GenBank: YP_003265308), *Synechococcus* thioesterase (GenBank: YP_001734428), or *Cyanothece* thioesterase (GenBank: YP_002377174).

The percent identity (homology) between two amino acid sequences can be determined as follows. First, the amino acid sequences are aligned using the BLAST 2 Sequences (Bl2seq) program from the stand-alone version of BLASTZ containing BLASTP version 2.0.14. This stand-alone version of BLASTZ can be obtained from Fish & Richardson's web site (e.g., www.fr.com/blast/) or the U.S. government's National Center for Biotechnology Information web site (www.ncbi.nlm.nih.gov). Instructions explaining how to use the Bl2seq program can be found in the readme file accompanying BLASTZ. Bl2seq performs a comparison between two amino acid sequences using the BLASTP algorithm. To compare two amino acid sequences, the options of Bl2seq are set as follows: -i is set to a file containing the first amino acid sequence to be compared (e.g., C:\seq1.txt); -j is set to a file containing the second amino acid sequence to be compared (e.g., C:\seq2.txt); -p is set to blastp; -o is set to any desired file name (e.g., C:\output.txt); and all other options are left at their default setting. For example, the following command can be used to generate an output file containing a comparison between two amino acid sequences: C:\Bl2seq-i c:\seq1.txt-j c:\seq2.txt-p blastp-o c:\output.txt. If the two compared sequences share homology (identity), then the designated output file will present those regions of homology as aligned sequences. If the two compared sequences do not share homology (identity), then the designated output file will not present aligned sequences. Similar procedures can be following for nucleic acid sequences except that blastn is used.

Once aligned, the number of matches is determined by counting the number of positions where an identical amino acid residue is presented in both sequences. The percent identity (homology) is determined by dividing the number of matches by the length of the full-length polypeptide amino acid sequence followed by multiplying the resulting value by 100. It is noted that the percent identity (homology) value is rounded to the nearest tenth. For example, 78.11, 78.12, 78.13, and 78.14 is rounded down to 78.1, while 78.15, 78.16, 78.17, 78.18, and 78.19 is rounded up to 78.2. It also is noted that the length value will always be an integer.

It will be appreciated that a number of nucleic acids can encode a polypeptide having a particular amino acid sequence. The degeneracy of the genetic code is well known to the art; i.e., for many amino acids, there is more than one nucleotide triplet that serves as the codon for the amino acid. For example, codons in the coding sequence for a given enzyme can be modified such that optimal expression in a particular species (e.g., bacteria or fungus) is obtained, using appropriate codon bias tables for that species.

Functional fragments of any of the enzymes described herein can also be used in the methods of the document. The term "functional fragment" as used herein refers to a peptide fragment of a protein that has at least 25% (e.g., at least: 30%; 40%; 50%; 60%; 70%; 75%; 80%; 85%; 90%; 95%; 98%; 99%; 100%; or even greater than 100%) of the activity of the corresponding mature, full-length, wild-type protein. The functional fragment can generally, but not always, be comprised of a continuous region of the protein, wherein the region has functional activity.

This document also provides (i) functional variants of the enzymes used in the methods of the document and (ii) functional variants of the functional fragments described above. Functional variants of the enzymes and functional fragments can contain additions, deletions, or substitutions relative to the corresponding wild-type sequences. Enzymes with substitutions will generally have not more than 50 (e.g., not more than one, two, three, four, five, six, seven, eight, nine, ten, 12, 15, 20, 25, 30, 35, 40, or 50) amino acid substitutions (e.g., conservative substitutions). This applies to any of the enzymes described herein and functional fragments. A conservative substitution is a substitution of one amino acid for another with similar characteristics. Conservative substitutions include substitutions within the following groups: valine, alanine and glycine; leucine, valine, and isoleucine; aspartic acid and glutamic acid; asparagine and glutamine; serine, cysteine, and threonine; lysine and arginine; and phenylalanine and tyrosine. The nonpolar hydrophobic amino acids include alanine, leucine, isoleucine, valine, proline, phenylalanine, tryptophan and methionine. The polar neutral amino acids include glycine, serine, threonine, cysteine, tyrosine, asparagine and glutamine. The positively charged (basic) amino acids include arginine, lysine and histidine. The negatively charged (acidic) amino acids include aspartic acid and glutamic acid. Any substitution of one member of the above-mentioned polar, basic or acidic groups by another member of the same group can be deemed a conservative substitution. By contrast, a nonconservative substitution is a substitution of one amino acid for another with dissimilar characteristics.

Deletion variants can lack one, two, three, four, five, six, seven, eight, nine, ten, 11, 12, 13, 14, 15, 16, 17, 18, 19, or 20 amino acid segments (of two or more amino acids) or non-contiguous single amino acids. Additions (addition variants) include fusion proteins containing: (a) any of the enzymes described herein or a fragment thereof; and (b) internal or terminal (C or N) irrelevant or heterologous amino acid sequences. In the context of such fusion proteins, the term "heterologous amino acid sequences" refers to an amino acid sequence other than (a). A heterologous sequence can be, for example a sequence used for purification of the recombinant protein (e.g., FLAG, polyhistidine (e.g., hexahistidine), hemagluttanin (HA), glutathione-S-transferase (GST), or maltosebinding protein (MBP)). Heterologous sequences also can be proteins useful as detectable markers, for example, luciferase, green fluorescent protein (GFP), or chloramphenicol acetyl transferase (CAT). In some embodiments, the fusion protein contains a signal sequence from another protein. In certain host cells (e.g., yeast host cells), expression and/or secretion of the target protein can be increased through use of a heterologous signal sequence. In some embodiments, the fusion protein can contain a carrier (e.g., KLH) useful, e.g., in eliciting an immune response for antibody generation) or ER or Golgi apparatus retention signals. Heterologous sequences can be of varying length and in some cases can be a longer sequences than the full-length target proteins to which the heterologous sequences are attached.

Recombinant hosts can naturally express none or some (e.g., one or more, two or more, three or more, four or more, five or more, or six or more) of the enzymes of the pathways described herein. Endogenous genes of the recombinant hosts also can be disrupted to prevent the formation of undesirable metabolites or prevent the loss of intermediates in the pathway through other enzymes acting on such intermediates. Recombinant hosts can be referred to as recombinant host cells, engineered cells, or engineered hosts. Thus, as described herein, recombinant hosts can include nucleic acids encoding one or more of a decarboxylase, a dehydrogenase, a desaturase, a hydratase, a thioesterase, or a coenzyme A transferase, as described in more detail below.

In addition, the production of isobutene can be performed in vitro using the isolated enzymes described herein, using a lysate (e.g., a cell lysate) from a host microorganism as a source of the enzymes, or using a plurality of lysates from different host microorganisms as the source of the enzymes.

In some embodiments, the (R)-3-hydroxy functional group is introduced into 3-methyl-but-2-enoyl-CoA by a R-specific enoyl-CoA hydratase enzyme classified, for example, under EC 4.2.1.- such as the gene product of phaJ. In some embodiments, the hydratase enzyme is the result of enzyme engineering, using the enzyme structure of phaJ, EC 4.2.1.119 and EC 4.2.1.18 to inform rational enzyme design.

In some embodiments, the vinyl group of isobutene is formed by a decarboxylating thioesterase such as CurM TE.

In some embodiments (FIG. 1), the central precursor to 3-methyl-but-2-enoyl-CoA, 3-methyl-2-oxo-butanoate, is converted to 3-methyl-2-hydroxy-butanoate by a 2-hydroxyacyl dehydrogenase such as EC 1.1.1.272; followed by conversion to 3-methyl-2-hydroxybutanoyl-CoA by a CoA transferase such as the gene product of GctAB; followed by conversion to 3-methyl-but-2-enoyl-CoA by a 2-hydroxyacyl-CoA dehydratase such as the gene product of HadBC and the initiator HadI; followed by conversion to 3-methyl-3-hydroxy-butanoyl-CoA by a (R)-specific enoyl-CoA hydratase classified, for example, under EC 4.2.1.- such as the gene product of phaJ; followed by conversion to 3-methyl-3-hydroxy-butanoate by a thioesterase classified, for example, under EC 3.1.2.- such as the gene product of tesA or tesB; followed by conversion to isobutene by a mevalonate diphosphate decarboxylase (classified, for example, under EC 4.1.1.33).

In some embodiments (FIG. 1), the central precursor to 3-methyl-but-2-enoyl-CoA, 3-methyl-2-oxo-butanoate, is converted to 3-methyl-2-hydroxy-butanoate by a 2-hydroxyacyl dehydrogenase such as EC 1.1.1.272; followed by conversion to 3-methyl-2-hydroxybutanoyl-CoA by a CoA transferase such as the gene product of GctAB; followed by conversion to 3-methyl-but-2-enoyl-CoA by a 2-hydroxy-acyl-CoA dehydratase such as the gene product of HadBC and the initiator HadI; followed by conversion to 3-methyl-3-hydroxy-butanoyl-CoA by a (R)-specific enoyl-CoA hydratase classified, for example, under EC 4.2.1.- such as the gene product of phaJ; followed by conversion to 3-methyl-3-hydroxy-butanoyl-ACP by a CoA:ACP 3-hydroxyacyltransferase such as the gene product of phaG or a phosphopantetheinyl transferase such as the gene product of sfp or svp; followed by conversion to 3-methyl-3-sulphoryl-butanoyl-ACP by a sulfotransferase such as CurM ST or OLS ST; followed by conversion to isobutene by a decarboxylating thioesterase such as CurM TE.

In some embodiments (FIG. 2), the central precursor to 3-methyl-but-2-enoyl-CoA, 4-methyl-2-oxo-pentanoate, is converted to 3-methylbutanoate by a 4-methyl-2-oxo-pentanoate dehydrogenase classified, for example, under EC 1.2.1.- such as the gene products of aceD and citL or classified under EC 1.2.7.7; followed by conversion to 3-methylcrotonyl-CoA by an isovaleryl-CoA dehydrogenase such as EC 1.3.8.4; followed by conversion to 3-methyl-3-hydroxy-butanoyl-CoA by a (R)-specific enoyl-CoA hydratase classified, for example, under EC 4.2.1.- such as the gene product of phaJ; followed by conversion to 3-methyl-3-hydroxy-butanoate by a thioesterase classified, for example, under EC 3.1.2.- such as the gene product of tesA or tesB; followed by conversion to isobutene by a mevalonate diphosphate decarboxylase (EC 4.1.1.33).

In some embodiments (FIG. 2), the central precursor to 3-methyl-but-2-enoyl-CoA, 4-methyl-2-oxo-pentanoate, is converted to 3-methylbutanoate by a 4-methyl-2-oxo-pentanoate dehydrogenase classified, for example, under EC 1.2.1.- such as the gene products of aceD and citL or classified under EC 1.2.7.7; followed by conversion to 3-methylcrotonyl-CoA by an isovaleryl-CoA dehydrogenase such as EC 1.3.8.4; followed by conversion to 3-methyl-3-hydroxy-butanoyl-CoA by a (R)-specific enoyl-CoA hydratase classified, for example, under EC 4.2.1.- such as the gene product of phaJ; followed by conversion to 3-methyl-3-hydroxy-butanoyl-ACP by a CoA:ACP 3-hydroxyacyltransferase such as the gene product of phaG or a phosphopantetheinyl transferase such as the gene product of sfp or svp; followed by conversion to 3-methyl-3-sulphoryl-butanoyl-ACP by a sulfotransferase such as CurM ST or OLS ST; followed by conversion to isobutene by a decarboxylating thioesterase such as CurM TE.

In some embodiments, the enzymes responsible for 3'-phosphoadenosine-5'-phosphosulfate (PAPS) synthesis classified under EC 2.7.7.4 and EC 2.7.1.25 are constitutively expressed in the host organisms.

Figure 2:
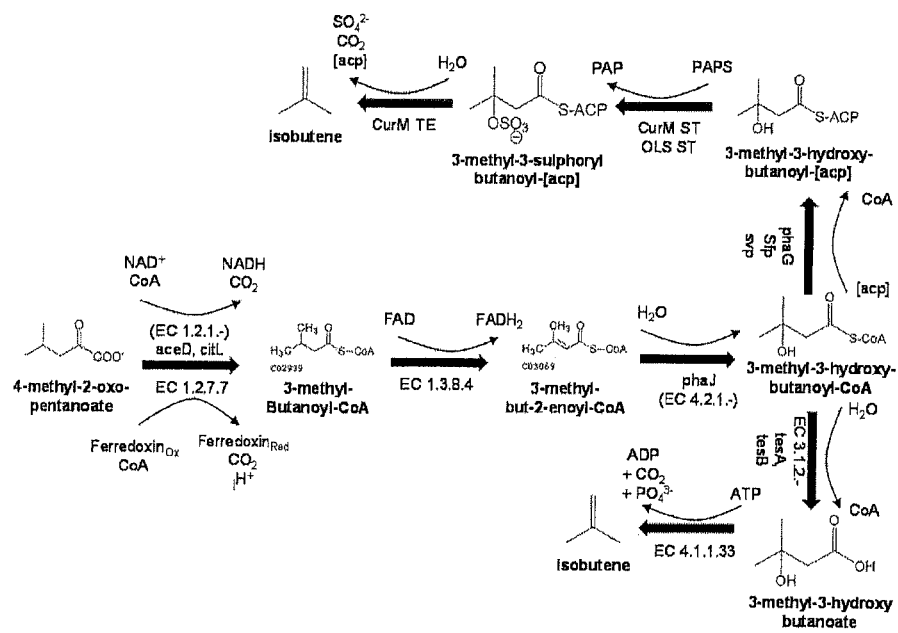
FIG. 2 is a schematic of exemplary biochemical pathways leading to isobutene using 4-methyl-2-oxopentanoate as a central precursor.

In some embodiments, the nucleic acids encoding the enzymes of the pathways described in FIG. 1 or 2 are introduced into a host microorganism that is either a prokaryote or eukaryote.

In some embodiments, the host microorganism is a prokaryote from the genus *Escherichia* such as *Escherichia coli*; from the genus Clostridia such as *Clostridium ljungdahlii*, *Clostridium autoethanogenum* or *Clostridium kluyveri*; from the genus Corynebacteria such as *Corynebacterium glutamicum*; from the genus *Cupriavidus* such as *Cupriavidus necator* or *Cupriavidus metallidurans*; from the genus Pseudomonas such as *Pseudomonas fluorescens* or *Pseudomonas putida*; from the genus Bacillus such as *Bacillus subtillis*; or from the genus Rhodococcus such as *Rhodococcus equi*.

In some embodiments, the host microorganism is a eukaryote from the genus Aspergillus such as *Aspergillus niger*; from the genus Saccharomyces such as *Saccharomyces cerevisiae*; from the genus Pichia such as *Pichia pastoris*; from the genus Yarrowia such as *Yarrowia lipolytica*; from the genus Issatchenkia such as *Issathenkia orientalis*; from the genus Debaryomyces such as *Debaryomyces hansenii*; from the genus Arxula such as *Arxula adenoinivorans*; or from the genus Kluyveromyces such as *Kluyveromyces lactis*.

In some embodiments, the fermentation strategy entails anaerobic, micro-aerobic or aerobic cultivation.

In some embodiments, a cell retention strategy using, for example, ceramic hollow fiber membranes is employed to achieve and maintain a high cell density during fermentation.

In some embodiments, the principal carbon source fed to the fermentation derives from biological or non-biological feedstocks.

In some embodiments, the biological feedstock is, or derives from, monosaccharides, disaccharides, hemicellulose such as levulinic acid and furfural, cellulose, lignocellulose, lignin, monosaccharides, disaccharides, triglycerides such as glycerol and fatty acids, agricultural waste or municipal waste.

In some embodiments, the non-biological feedstock is, or derives from, either natural gas, syngas, $CO_2/H_2$, methanol, ethanol, non-volatile residue (NVR) caustic wash from cyclohexane oxidation or waste streams from the chemical and petrochemical industries.

In some embodiments, substantially pure cultures of recombinant host microorganisms are provided. As used herein, a "substantially pure culture" of a recombinant host microorganism is a culture of that microorganism in which less than about 40% (i.e., less than about: 35%; 30%; 25%; 20%; 15%; 10%; 5%; 2%; 1%; 0.5%; 0.25%; 0.1%; 0.01%; 0.001%; 0.0001%; or even less) of the total number of viable cells in the culture are viable cells other than the recombinant microorganism, e.g., bacterial, fungal (including yeast), mycoplasmal, or protozoan cells. The term "about" in this context means that the relevant percentage can be 15% of the specified percentage above or below the specified percentage. Thus, for example, about 20% can be 17% to 23%. Such a culture of recombinant microorganisms includes the cells and a growth, storage, or transport medium. Media can be liquid, semi-solid (e.g., gelatinous media), or frozen. The culture includes the cells growing in the liquid or in/on the semi-solid medium or being stored or transported in a storage or transport medium, including a frozen storage or transport medium. The cultures are in a culture vessel or storage vessel or substrate (e.g., a culture dish, flask, or tube or a storage vial or tube).

EXAMPLE

Enzyme Activity of R-Specific Enoyl-CoA
Hydratase Accepting
3-methyl-3-hydroxybutanoyl-CoA as Substrate A C-terminal His-tagged pilaf gene from *Aeromonas punctata*, which encodes a R-specific enoyl-CoA hydratase (SEQ ID NO:2, see FIG. 3) was cloned into a pE23a expression vector under the T7 promoter. The expression vector was transformed into a BL21[DE3] *E. coli* host. The resulting recombinant *E. coli* strain was cultivated at 30° C. in a 1 L shake flask culture containing 100 mL Luria Broth media, with shaking at 200 rpm. The culture was induced using 1 mM IPTG for 2 hours.

The pellet from each of the induced shake flask cultures was harvested by centrifugation. Each pellet was resuspended in 20 mM HEPES (pH=7.2 [-]), 1 mM PMSF and 29 units benzonase, and lysed via sonication. The cell debris was separated from the supernatant via centrifugation and filtered using a 0.2 µm filter. The pilaf enzyme was purified from the supernatant using Ni-affinity chromatography and concentrated to 1.25 mg/mL.

Figure 5:
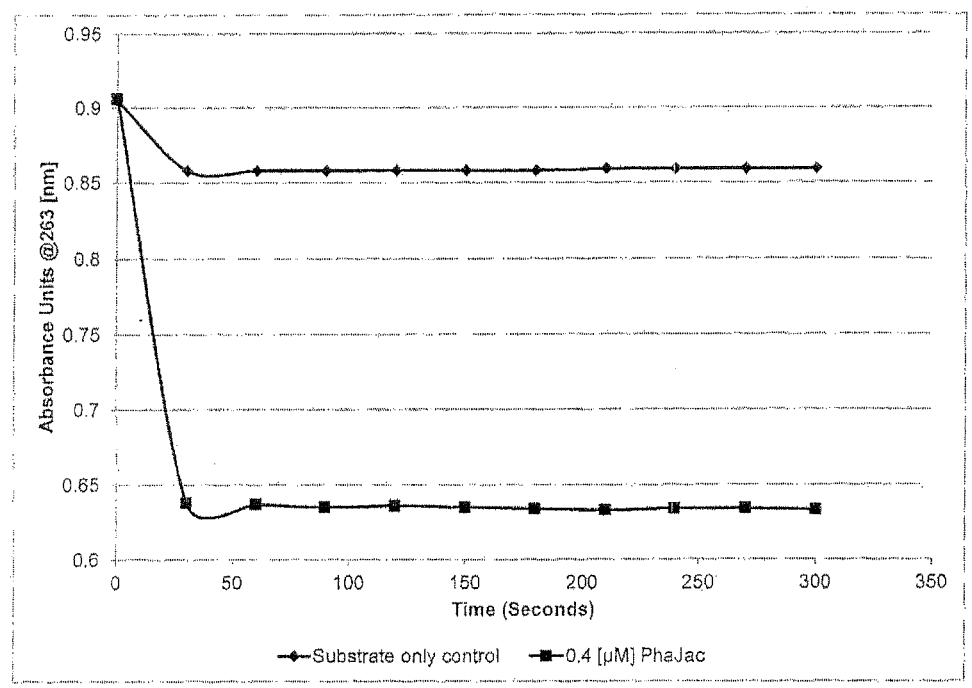
FIG. 5 is a graph of the absorbance units of crotonyl-CoA (substrate) over time in a spectrophotometric enzyme assay in the forward (hydrating) direction for an enoyl-CoA hydratase encoded by phaJ.

The native enzyme activity assay in the forward (hydration) direction was undertaken in a buffer composed of 10 mM ammonium acetate (pH=8) and 1 mM of crotonyl-CoA (also known as 2-butenoyl-CoA) (Sigma-Aldrich) at 30° C. The enzyme activity assay reaction was initiated by adding 0.4 µM of purified enoyl-CoA hydratase to the assay buffer containing the substrate. The enoyl-CoA hydratase accepted crotonyl-CoA as substrate as confirmed via spectrophotometry at 263 nm at 30° C. The substrate only control showed minimal spontaneous hydration of crotonyl-CoA as determined by spectrophotometry at 263 nm. See FIG. 5.

The native enzyme activity assay in the reverse (dehydration) direction was undertaken in a buffer composed of 10 mM ammonium acetate (pH=8) and 1 mM of racemic 3-hydroxybutanoyl-CoA. The enzyme activity assay reaction was initiated by adding 5 µM of purified enoyl-CoA hydratase to the assay buffer containing the substrate and incubated at 30° C. for 1 hour. The enoyl-CoA hydratase accepted 3-hydroxybutanoyl-CoA as substrate as confirmed via LC-MS. The substrate only control showed negligible spontaneous dehydration of 3-hydroxybutanoyl-CoA. As demonstrated previously (Lan and Liao, *Proc. Natl. Acad. Sci. USA*, 2012, 109(16), 6018-6023), the enoyl-CoA hydratase encoded by pilaf is reversible, though favors the forward (hydration) direction. See FIG. 6.

The non-native enzyme activity assay in the reverse (dehydration) direction was undertaken in a buffer composed of 10 mM ammonium acetate (pH=8) and 1 mM of 3-methyl-3-hydroxybutanoyl-CoA. The enzyme activity assay reaction was initiated by adding 5 µM of purified enoyl-CoA hydratase to the assay buffer containing the substrate and incubated at 30° C. for 1 hour. The enzyme encoded by phaJ accepted 3-methyl-3-hydroxybutanoyl-CoA as substrate as confirmed via LC-MS. The substrate only control showed no spontaneous dehydration of 3-methyl-3-hydroxybutanoyl-CoA. See FIG. 7.

The enoyl-CoA hydratase encoded by pilaf from *Aeromonas punctata* accepted 3-methyl-3-hydroxybutanoyl-CoA as substrate in the dehydration direction. Given the reversibility of the enzyme reaction and the favored hydration direction, the enoyl-CoA hydratase encoded by pilaf from *Aeromonas punctata* accepts 3-methyl-but-2-enoyl-CoA as substrate.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

---

What is claimed is:

1. A method for synthesizing isobutene, said method comprising enzymatically converting 3-methyl-but-2-enoyl-CoA to form to 3-methyl-3-hydroxy-butanoyl-CoA using a R-specific enoyl-CoA hydratase with at least 90% sequence identity to SEQ ID NO:1, 2 or 3 and which is capable of converting 3-methyl-but-2-enoyl-CoA to 3-methyl-3-hydroxy-butanoyl-CoA, enzymatically converting 3-methyl-3-hydroxy-butanoyl-CoA to 3-methyl-3-sulphoryl-butanoyl-ACP using a CoA:ACP 3-hydroxyacyltransferase or phosphopantetheinyl transferase capable of converting 3-methyl-3-hydroxy-butanoyl-CoA to 3-methyl-3-hydroxy-butanoyl-ACP and a sulfotransferase capable of converting 3-methyl-3-hydroxy-butanoyl-ACP to 3-methyl-3-sulpho-ryl-butanoyl-ACP, and enzymatically converting 3-methyl-3-sulphoryl-butanoyl-ACP to isobutene using a decarboxylating thioesterase which has at least 90% sequence identity to Lyngbya majuscula chain A, thioesterase from the Curacin biosynthetic pathway comprising SEQ ID NO:4 and is capable of converting 3-methyl-3-sulphoryl-butanoyl-ACP to isobutene or a decarboxylating thioesterase capable of converting 3-methyl-3-sulphoryl-butanoyl-ACP to isobutene derived from *Pseudomonas entomophila, Haliangium ochraceum, Synechococcus,* or *Cyanothece*.

2. The method according to claim 1, where the decarboxylating thioesterase has at least 95% sequence identity to the amino acid sequence set forth in SEQ ID NO: 4.

3. The method according to claim 1, where the decarboxylating thioesterase has at least 90% sequence identity to the amino acid sequence set forth in SEQ ID NO:4.

4. The method of claim 1, wherein the method is performed using isolated enzymes.

5. The method of claim 1, wherein said method is performed using cell lysates comprising said enzymes.

6. The method of claim 1, wherein said method is performed in a host cell to produce isobutene by fermentation.

7. The method of claim 6, wherein the host cell is either a prokaryote or eukaryote.

8. The method according to claim 7, where the prokaryotic host cell is from the genus *Escherichia*; from the genus *Clostridium*; from the genus *Corynebacterium*; from the genus *Cupriavidus*; from the genus *Pseudomonas*; from the genus *Bacillus*; or from the genus *Rhodococcus*.

9. The method according to claim 8, wherein the prokaryotic host cell is *Escherichia coli; Clostridium ljungdahlii, Clostridium autoethanogenum, Clostridium kluyveri, Corynebacterium glutamicum, Cupriavidus necator, Cupriavidus metallidurans, Pseudomonas fluorescens, Pseudomonas putida, Bacillus subtillis* or *Rhodococcus equi*.

10. The method according to claim 7, where the eukaryotic host cell is from the genus *Aspergillus*; from the genus *Saccharomyces*; from the genus *Pichia*; from the genus *Yarrowia*; from the genus *Issatchenkia*; from the genus *Debaryomyces*; from the genus *Arxula*; or from the genus *Kluyveromyces*.

11. The method according to claim 10, wherein the eukaryotic host cell is *Aspergillus niger, Saccharomyces cerevisiae, Pichia pastoris, Yarrowia lipolytica, Issathenkia orientalis, Debaryomyces hansenii, Arxula adenoinivorans,* or *Kluyveromyces lactis.*

12. The method according to claim 6, further comprising culturing the host cell in an anaerobic, micro-aerobic or aerobic cultivation.

13. The method according to claim 6, further comprising culturing the host cell in a ceramic hollow fiber membrane to achieve and maintain a high cell density during fermentation.

14. The method according to claim 6, further comprising culturing the host cell in a fermentation having a principal carbon source fed to the fermentation derived from biological or non-biological feedstocks.

15. The method according to claim 14, where the biological feedstock is glycerol, levulinic acid, hemicellulose, cellulose, lignocellulose, lignin, monosaccharides, disaccharides, triglycerides or municipal waste.

16. The method according to claim 14, where the non-biological feedstock is natural gas, syngas, carbon monoxide, $CO_2/H_2$, methanol, ethanol or waste stream from chemical or petrochemical industries.

17. The method according to claim 1, where the decarboxylating thioesterase comprises the amino acid sequence set forth in SEQ ID NO: 4.

* * * * *